United States Patent
Xiao et al.

(10) Patent No.: US 12,324,735 B2
(45) Date of Patent: Jun. 10, 2025

(54) STENT GRAFT WITH VARIABLE COVERAGE OF WAVY RINGS

(71) Applicant: LIFETECH SCIENTIFIC (SHENZHEN) CO., LTD, Shenzhen (CN)

(72) Inventors: Benhao Xiao, Shenzhen (CN); Caiping Liu, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 0 days.

(21) Appl. No.: 18/297,885

(22) Filed: Apr. 10, 2023

(65) Prior Publication Data
US 2023/0240832 A1  Aug. 3, 2023

Related U.S. Application Data

(63) Continuation of application No. 16/954,328, filed as application No. PCT/CN2018/120312 on Dec. 11, 2018, now abandoned.

(30) Foreign Application Priority Data

Dec. 27, 2017  (CN) .......................... 201711446219.4

(51) Int. Cl.
*A61F 2/07* (2013.01)
*A61F 2/915* (2013.01)

(52) U.S. Cl.
CPC ...... *A61F 2/07* (2013.01); *A61F 2002/91516* (2013.01); *A61F 2220/0016* (2013.01); *A61F 2240/001* (2013.01)

(58) Field of Classification Search
CPC ........................................................ A61F 2/82
See application file for complete search history.

(56) References Cited

U.S. PATENT DOCUMENTS 5,800,520 A * 9/1998 Fogarty ................... A61F 2/915
                                                            623/1.37
8,663,313 B2   3/2014 Boismier et al.
(Continued)

FOREIGN PATENT DOCUMENTS

CN    2817768 Y   9/2006
CN    2822554 Y   10/2006
(Continued)

OTHER PUBLICATIONS

International Search Report issued on Mar. 1, 2019 and Written Opinion in corresponding International application No. PCT/CN2018/120312; 11 pages.
(Continued)

*Primary Examiner* — Jacqueline Wozniki
(74) *Attorney, Agent, or Firm* — Maier & Maier, PLLC

(57) ABSTRACT

A stent graft; the stent graft is provided in the axial direction thereof with at least one Region T, and the Region T includes a plurality of wavy rings; in the circumferential direction, the Region T includes a region A and a Region B that is connected to the region A, the ratio of the area of the region A to the area of the Region T being 1/4-2/3, the ratio of the coverage rate of the wavy rings in the region A to the coverage rate of the wavy rings in the Region B being 1/5-9/10, and the ratio of the coverage rate of the wavy rings within any circular region having a diameter of 20 mm within the region A to the coverage rate of the wavy rings in the region A being 0.7-1.3.

20 Claims, 8 Drawing Sheets

(56) References Cited

U.S. PATENT DOCUMENTS

| | | | |
|---|---|---|---|
| 8,992,595 B2* | 3/2015 | Parsons | A61F 2/07 623/1.13 |
| 2002/0055770 A1 | 5/2002 | Doran et al. | |
| 2002/0103529 A1 | 8/2002 | Pinchasik et al. | |
| 2004/0015228 A1 | 1/2004 | Lombardi et al. | |
| 2004/0088044 A1 | 5/2004 | Brown et al. | |
| 2007/0191926 A1 | 8/2007 | Nikanorov et al. | |
| 2007/0260304 A1 | 11/2007 | Gregorich et al. | |
| 2008/0004690 A1* | 1/2008 | Robaina | A61F 2/915 623/1.42 |
| 2008/0114445 A1 | 5/2008 | Melsheimer et al. | |
| 2009/0036970 A1* | 2/2009 | Ma | A61F 2/91 623/1.35 |
| 2009/0069880 A1 | 3/2009 | Vonderwalde et al. | |
| 2009/0157164 A1 | 6/2009 | McKinsey et al. | |
| 2010/0249902 A1 | 9/2010 | Sakai et al. | |
| 2014/0243951 A1 | 8/2014 | Orr | |
| 2014/0296975 A1 | 10/2014 | Tegels et al. | |
| 2015/0250626 A1 | 9/2015 | Fischer et al. | |
| 2017/0273811 A1* | 9/2017 | Ikeuchi | A61F 2/95 |
| 2020/0330215 A1 | 10/2020 | Xiao et al. | |
| 2021/0077245 A1 | 3/2021 | Xiao et al. | |

FOREIGN PATENT DOCUMENTS

| | | |
|---|---|---|
| CN | 201438978 U | 4/2010 |
| CN | 203107339 U | 8/2013 |
| CN | 107242917 A | 10/2017 |
| EP | 3042631 B1 | 2/2020 |

OTHER PUBLICATIONS

Extended European Search Report issued on Feb. 16, 2021, in connection with corresponding EP Application No. 18894891.3; 10 pages.

First Chinese Office Action issued on Jun. 24, 2020, in connection with corresponding CN Application No. 201711446219.4 (13 pp., including machine-generated English translation).

First Chinese Search Report issued on Jun. 16, 2020, in connection with corresponding CN Application No. 201711446219.4 (2 pp.).

Chinese Supplemental Search Report issued on Dec. 8, 2020, in connection with corresponding CN Application No. 201711446219.4 (1 pp.).

Chinese Notification to Grant Patent Right for Invention issued on Dec. 17, 2020, in connection with corresponding CN Application No. 201711446219.4 (3 pp., including machine-generated English translation).

Office Action issued on Jul. 17, 2024, in corresponding European Application No. 18 894 891.3, 4 pages.

* cited by examiner

STENT GRAFT WITH VARIABLE COVERAGE OF WAVY RINGS

CROSS-REFERENCE TO RELATED APPLICATIONS

This application is a continuation of U.S. application Ser. No. 16/954,328, filed on Jun. 16, 2020, which is a national phase of International Application No. PCT/CN2018/120312, filed on Dec. 11, 2018, which claims priority to Chinese Application No. 201711446219.4, filed on Dec. 27, 2017, the contents of all of which are herein incorporated by reference.

FIELD

The embodiments relate to the field of medical apparatuses, and, in particular, to a stent graft.

BACKGROUND

Over the past decade, endovascular stent-grafts for aortic dissections have been widely used in lesions such as thoracic and abdominal aortic aneurysms and arterial dissections, and have become a first-line treatment with definite efficacy, less trauma, faster recovery, and fewer complications. However, for special lesions such as aortic arch, celiac trunk, bilateral renal artery or superior mesenteric artery, the use of stent grafts can affect the blood supply to the arterial branch vessels. In view of this, the stent graft is usually opened in situ by laser or mechanically during the operation, so that the stent graft produces an expected hole, and then the branch stent is transported to the hole and docked with the stent graft. Such a therapeutic regimen overcomes the dependence on the anatomical structure of human branch vessels.

In the prior art, when the stent graft is opened in situ, there are some problems that the window size is difficult to meet the requirements, or the window edge support is poor.

SUMMARY

The embodiments provide a stent graft suitable for in-situ fenestration to overcome the defects in the prior art.

In order to overcome the defects in the prior art, exemplary solutions are provided as follows.

Provided is a stent graft, where at least one region T is disposed in an axial direction of the stent graft; the region T includes a plurality of wavy rings; the region T further includes, in a circumferential direction, a region A and a region B connected with the region A; the ratio of the area of the region A to the area of the region T ranges from 1/4 to 2/3; the ratio of the coverage rate of the wavy rings in the region A to the coverage rate of the wavy rings in the region B ranges from 1/5 to 9/10; and the ratio of the coverage rate of the wavy rings in any circular region with a diameter of 20 mm within the region A to the coverage rate of the wavy rings in the region A ranges from 0.7 to 1.3.

In the stent graft, the ratio of the area of the region A to the area of the region T ranges from 1/3 to 1/2; the ratio of the coverage rate of the wavy rings in the region A to the coverage rate of the wavy rings in the region B ranges from 2/5 to 9/10; and the ratio of the coverage rate of the wavy rings in any circular region with a diameter of 20 mm within the region A to the coverage rate of the wavy rings in the region A ranges from 0.9 to 1.1.

In the stent graft, the region A includes a plurality of first wavy segments arranged in a spaced manner in the axial direction, the wave height of the first wavy segment is L1, the spacing between the adjacent first wavy segments is L2, and L1/L2 is greater than or equal to 1/4 and less than or equal to 3.

In the stent graft, L1 is greater than or equal to 4 mm and less than or equal to 12 mm.

In the stent graft, the wave heights of the plurality of first wavy segments are equal, and the spacings between the adjacent first wavy segments are equal.

In the stent graft, the region B includes keel regions and non-keel regions that are distributed in the circumferential direction, each non-keel region includes a plurality of second wavy segments distributed in the axial direction, each keel region includes a plurality of third wavy segments distributed in the axial direction, and the wave heights of the third wavy segments are greater than the wave heights of the first wavy segments and the wave heights of the second wavy segments.

In the stent graft, the ratio of the wave height of the second wavy segment to the wave height of the first wavy segment ranges from 0.8 to 1.2, and the ratio of the spacing between the adjacent second wavy segments to the spacing between the adjacent first wavy segments ranges from 0.8 to 1.2.

In the stent graft, the wave included angle of the third wavy segment is less than the wave included angle of the first wavy segment and the wave included angle of the second wavy segment.

In the stent graft, the included angle of the keel region in the circumferential direction is 15°-45°.

In the stent graft, the stent graft further includes an anchoring bare stent located at at least one end of the stent graft.

Thus a stent graft of the embodiments can have at least the following beneficial effects: the stent graft has a region A and a region B that are distributed in the circumferential direction, the ratio of the coverage rate of the wavy rings in the region A to the coverage rate of the wavy rings in the region B is 1/5-9/10, and the coverage rate of the wavy rings in the region A is relatively low, so that the region A is more favorable for fenestration; and the axial supporting effect of the whole region T can be enhanced by the relatively high coverage rate of the wavy rings in the region B.

BRIEF DESCRIPTION OF THE DRAWINGS

The embodiments will be further described in combination with accompanying drawings. In the drawings.

DETAILED DESCRIPTION OF THE EMBODIMENTS

In order that the technical features, objects and effects of the embodiments may be more clearly appreciated, embodiments thereof will now be described in detail with reference to the accompanying drawings.

It should be noted that "distal" and "proximal" are used as orientation words, which are customary terms in the field of interventional medical apparatuses, where the "distal" means an end away from an operator during a surgical procedure, and the "proximal" means an end close to the operator during the surgical procedure. An axial direction refers to a direction which is parallel to the connecting line of a distal center and a proximal center of a medical apparatus; a radial direction refers to a direction perpendicular to the axial direction; and the distance from the axis refers to the distance reaching the axis in the radial direction.

Figure 1:
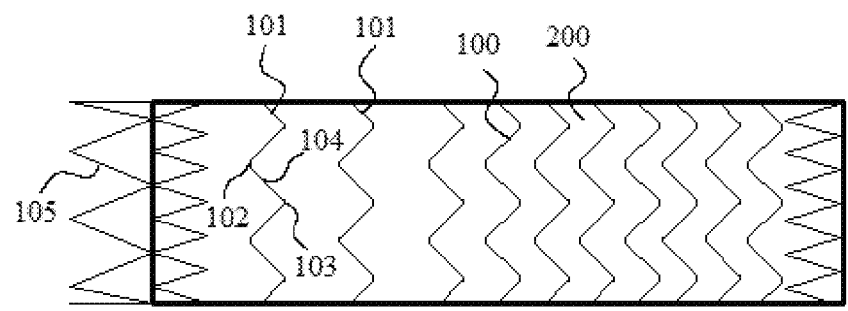
FIG. 1 is a schematic diagram of a stent graft provided by a first exemplary embodiment.

As shown in FIG. 1, a first exemplary embodiment provides a stent graft which is substantially of an open-ended and hollow tubular structure, a tube cavity of the stent graft forming a blood flow channel. The stent graft mainly includes a bare stent 100 and covering membranes 200 fixed to the bare stent 100.

The bare stent 100 is made of a material having good biocompatibility, such as nickel titanium, stainless steel, or the like. The bare stent 100 includes a plurality of wavy rings 101 that are sequentially arranged in a spaced manner, For example arranged in a parallelly spaced manner, from the proximal end to the distal end. It can be appreciated that, in other embodiments, the bare stent 100 may be of other structures, such as a mesh-like structure.

The covering membranes 200 are substantially middle-closed and open-ended tube cavity structures and made of high molecular materials with good biocompatibility, such as e-PTFE, PET, or the like. The covering membranes 200 are fixed to the plurality of wavy rings 101 to connect the plurality of wavy rings 101 and are enclosed to form a tube cavity with a longitudinal axis, and the tube cavity serves as a channel through which blood flows.

Each wavy ring 101 is a closed cylindrical structure, and includes a plurality of proximal vertexes 102, a plurality of distal vertexes 103, and supporting bodies 104 connecting the adjacent proximal vertexes 102 and distal vertexes 103, and the proximal vertexes 102 and distal vertexes 103 are wave crests and troughs of corresponding waves, respectively. The plurality of wavy rings 101 have the same or similar wavy shapes, for example, the wavy rings 101 may be of Z-shaped waves, M-shaped waves, V-shaped waves or sinusoidal wave structures, or of other structures that are radially compressible to a very small diameter. The embodiment does not limit the structures of the wavy rings 101, the wave shapes of the wavy rings 101 may be set as required or desired, and the number of waves and the heights of the waves in each wavy ring 101 may be set as required or desired.

The stent graft may be prepared as follows: weaving a metal wire into a required wave shape, where the metal wire may be a nickel-titanium alloy wire with a wire diameter of, for example, 0.35 mm; and after heat setting, sleeving two end portions of the metal wire with a steel jacket and fixing by mechanical pressing so that the metal wire and the steel jacket are connected and fastened to form a wavy ring. After all the wavy rings are manufactured, surfaces of the wavy rings 101 which are sequentially arranged in a spaced manner are covered with membranes. For example, inner surfaces and outer surfaces of the wavy rings 101 may be integrally covered with e-PTFE membranes, the wavy rings 101 are located between two covering membranes 200, and the e-PTFE covering membranes of an inner layer and an outer layer are bonded together by high-temperature pressing, thereby fixing the wavy rings 101 between the two covering membranes. It will be appreciated that in other embodiments the wavy rings 101 may also be sutured to a PET membrane.

Further, when formed by integrally cutting a metal tube, the wavy rings 101 are not required to be fixedly connected by the steel jacket. Alternatively, the wavy ring may be formed by welding two end points of the metal wire.

Figure 2:
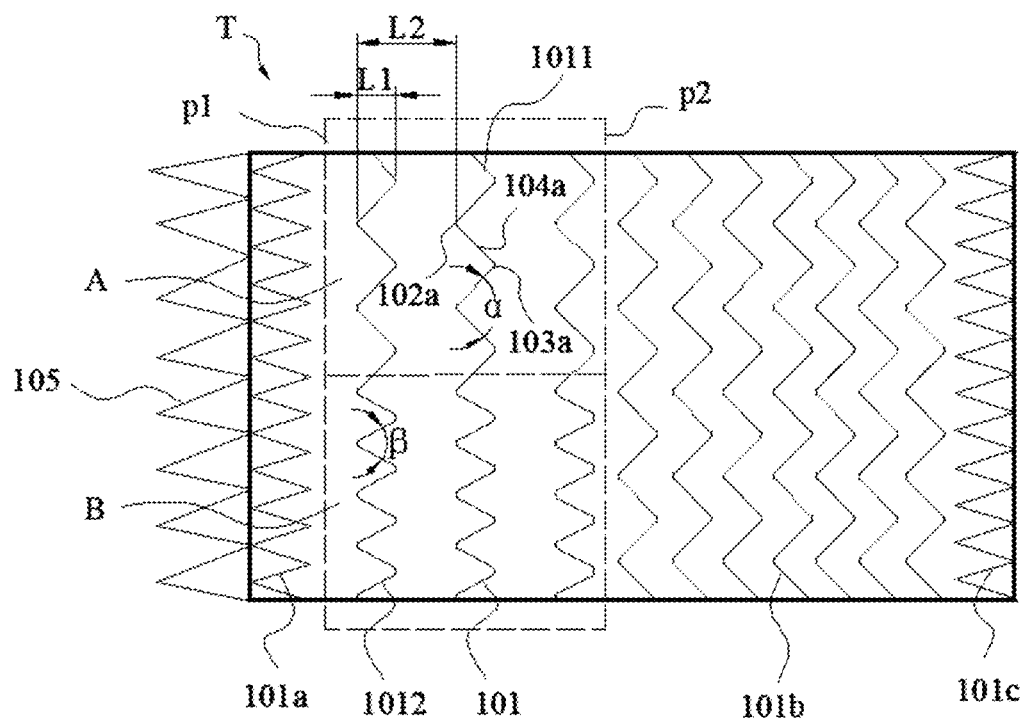
FIG. 2 is a radially expanded view of the stent graft shown in FIG. 1.

FIG. 2 is a radially expanded view of the stent graft shown in FIG. 1. As shown in FIG. 2, at least one region T is disposed in the axial direction of the stent graft, the region T is partitioned by two planes p1 and p2 respectively perpendicular to the axial direction of the stent graft, and a region shown by a dotted line frame in FIG. 2 is the region T which corresponds to a branch vessel on an aorta. A region T may correspond to one or more branch vessels, or multiple regions T may correspond to branch vessels at different positions, respectively. In other embodiments the planes p1 and p2 may be not perpendicular to the axial direction of the stent graft.

The region T includes, in a circumferential direction, a region A and a region B connected with the region A. The coverage rate of the wavy rings in the region A is less than the coverage rate of the wavy rings in the region B. For example, the ratio of the coverage rate of the wavy rings in the region A to the coverage rate of the wavy rings in the region B is 1/5-9/10, the ratio of the area of the region A to the area of the region T is within the range of 1/4-2/3, and the ratio of the coverage rate of the wavy rings in a circular region with the diameter of 20 mm that is arbitrarily selected in the region A to the coverage rate of the wavy rings in the region A is 0.7-1.3. The coverage rate of the wavy rings in a certain region of the stent graft defines the percentage of the wavy rings in the region on the stent graft, and the coverage rate of the wavy rings is calculated in a way that the surface area of the wavy ring projected onto an inner wall of a tube cavity of the stent graft in a certain region is divided by the surface area of the inner wall of the tube cavity of the stent graft and multiplied by 100%.

When the coverage rate of the wavy rings in a certain region is higher, the wavy rings distributed in the region is denser, axial supporting force of the stent graft can be well guaranteed, and the stent graft is prevented from retracting into a tumor cavity. However, since the wavy rings limit the fenestration size, the fenestration size can hardly meet the requirement on the size of the branch vessel. When the coverage rate of the wavy rings in the region is lower, the wavy rings are sparsely distributed in the region, and the wavy rings do not limit the fenestration size. However, the axial supporting force of the region is poor, and the stent graft is prone to shortening in the blood vessel, resulting in that the stent graft possibly retracts into the tumor cavity. Meanwhile, the lower coverage rate of the wavy rings also easily leads the edge of a window to be far away from the wavy rings after fenestration, and with small supporting force from a window region, it is difficult to provide sufficient anchoring force for the branch stent implanted in the window position, easily leading to the separation of the branch stent from the stent graft; and without the limitation of the wavy rings in the fenestration position, the window is further expanded under the action of radial force of the branch stent, finally resulting in the separation of the branch stent from the stent graft. According to an embodiment, by arranging the region A and the region B with different coverage rates of the wavy rings in the circumferential direction, and by adjusting the ratio of the area of the region A to the area of the region B and adjusting the ratio of the coverage rate of the wavy rings in the region A to the coverage rate of the wavy rings in the region B, the region B of the stent graft can meet the axial supporting force to prevent the stent graft from shortening into the tumor cavity, and the region A can meet the requirements of fenestration. In addition, the ratio of the coverage rate of the wavy rings in the circular region with the diameter of 20 mm that is arbitrarily selected in the region A to the coverage rate of the wavy rings in the region A is 0.7-1.3, and the requirements of fenestration can also be well met in each position of the region A, thereby improving the adaptability of the stent graft.

Further, the ratio of the coverage rate of the wavy rings in the region A to the coverage rate of the wavy rings in the region B is 2/5-9/10, the ratio of the area of the region A to the area of the region T is 1/3-1/2, and the ratio of the coverage rate of the wavy rings in the circular region with a diameter of 20 mm that is arbitrarily selected in the region A to the coverage rate of the wavy rings in the region A is 0.9-1.1, so that the performance of the stent graft can be well guaranteed.

Referring to FIG. 2, the wavy ring 101 includes a first wavy segment located in the region A, where the first wavy segment 1101 includes a plurality of first proximal vertexes 102a, a plurality of first distal vertexes 103a, and first supporting bodies 104a connecting the adjacent first proximal vertexes 102a and first distal vertexes 103a. In the embodiment, the plurality of first distal vertexes 103a are located in the same plane perpendicular to the longitudinal axis.

The wave height of the first wavy segment 1011 is L1, the axial distance between the proximal vertex 102a of the first wavy segment 1011 and the corresponding proximal vertex 102a of the adjacent proximal vertex 102a is L2, and L1 and L2 meet the condition that L1/L2 is greater than or equal to 1/4 and less than or equal to 3. The wave height of the first wavy segment 1011 refers to the distance between the first proximal vertex 102a and the first distal vertex 103a in the axial direction. If L1/L2 is less than 1/4, L1 is relatively too small, and L2 is relatively too large, easily causing a fenestration edge to be away from the wavy ring 101 and a failure to provide sufficient supporting force for the fenestration edge by of the wavy ring 101, and finally causing separation of two stents. If L1/L2 is greater than 3, L1 is relatively too large, and L2 is relatively too small, so that the fenestration size will be limited, and the fenestration is not facilitated. For example, L1 is greater than or equal to 4 mm and less than or equal to 12 mm. In the embodiment, the wave heights L1 of the plurality of first wavy segments are equal, and the spacings L2 between every two adjacent first wavy segments are equal.

The plurality of first wavy segments in the region A are arranged in a spaced manner in the axial direction, and the phase difference between two adjacent first wavy segments is 0-45°. In the embodiment, the phase difference between two adjacent first wavy segments is zero. The phase difference of zero means that a connecting line between a first proximal vertex 102a of the first wavy segment 1011 and a first proximal vertex 102a of an adjacent first wavy segment is parallel to the axis of the stent graft.

The wavy ring 101 further includes a second wavy segment 1012 located in the region B, the wave included angle α of the first wavy segment 1011 is greater than the wave included angle β of the second wavy segment 1012, and the wave height of the first wavy segment 1011 is the same as the wave height of the second wavy segment 1012. The wave included angle refers to an included angle between supporting bodies 104 connected to two sides of the same proximal vertex 102 or distal vertex 103; and the wave height refers to the relative distance between the adjacent proximal vertex 102 and distal vertex 103.

The spacing between two adjacent first wavy segments 1011 and the spacing between two adjacent second wavy segments 1012 may be set as desired, and the wave shapes, the number of waves, the wave heights, and the wave included angles of the first wavy segments 1011 and the second wavy segments 1012 may be set as desired.

Referring to FIG. 2, the stent graft further includes at least one proximal wavy ring 101a and at least one distal wavy ring 101c that are located at two ends of the region T, respectively.

The coverage rate of the wavy rings in the region where the at least one proximal wavy ring 101a is located is greater than the coverage rate of the wavy rings in the region T, the coverage rate of the wavy rings in the region where the at least one distal wavy ring 101c is located is greater than the coverage rate of the wavy rings in the region T, that is, the coverage rates of the wavy rings in the proximal region and the distal region are greater than the coverage rate of the wavy rings in the middle region of the stent graft. Since the coverage rates of the wavy rings at the two ends of the stent graft are high, the axial supporting effects at the two ends of the stent graft may be enhanced, and the two ends of the stent graft are prevented from causing the stent graft to swing under the impact of a blood flow.

The stent graft further includes at least one non-end wavy ring 101b located between the region T and the distal wavy ring 101c.

The coverage rate of the wavy rings in the region where the at least one non-end wavy ring 101b is located is greater than the coverage rate of the wavy rings in the region T, so as to enhance the integral axial supporting effect of the stent graft. Meanwhile, the coverage rate of the wavy rings in the region where the at least one non-end wavy ring 101b is located is less than the coverage rate of the wavy rings in the region where the at least one distal wavy ring 101c is located.

The proximal wavy ring 101a, the non-end wavy ring 101b and the distal wavy ring 101c are made of materials having good biocompatibility, such as nickel titanium, stainless steel or the like. The proximal wavy ring 101a, the non-end wavy ring 101b, and the distal wavy ring 101c are of closed cylindrical structures. The proximal wavy ring 101a, the non-end wavy ring 101b and the distal wavy ring 101c may be of Z-shaped wave, M-shaped wave, V-shaped wave or sinusoidal wave structures, or of other structures that are radially compressible to a very small diameter.

It will be appreciated that not only the numbers of the proximal wavy ring 101a, the non-end wavy ring 101b, and the distal wavy ring 101c may be set as desired, but also the wave shapes, the number of waves, and the wave heights of the proximal wavy ring 101a, the non-end wavy ring 101b and the distal wavy ring 101c may be set as desired.

The stent graft further includes an anchoring bare stent 105 located at one or two ends of the stent graft and connected with the proximal wavy ring 101a or the distal wavy ring 101c.

Figure 3:
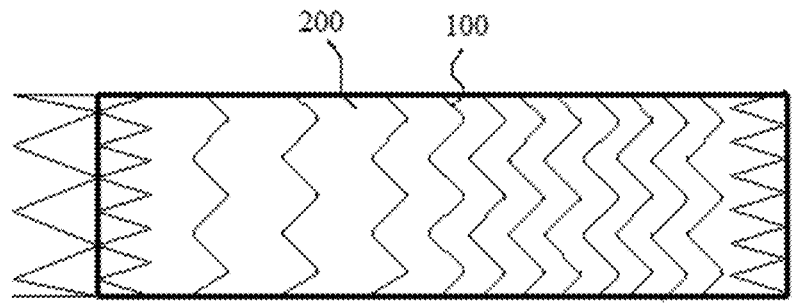
FIG. 3 is a schematic diagram of a stent graft provided by a second exemplary embodiment.
Figure 4:
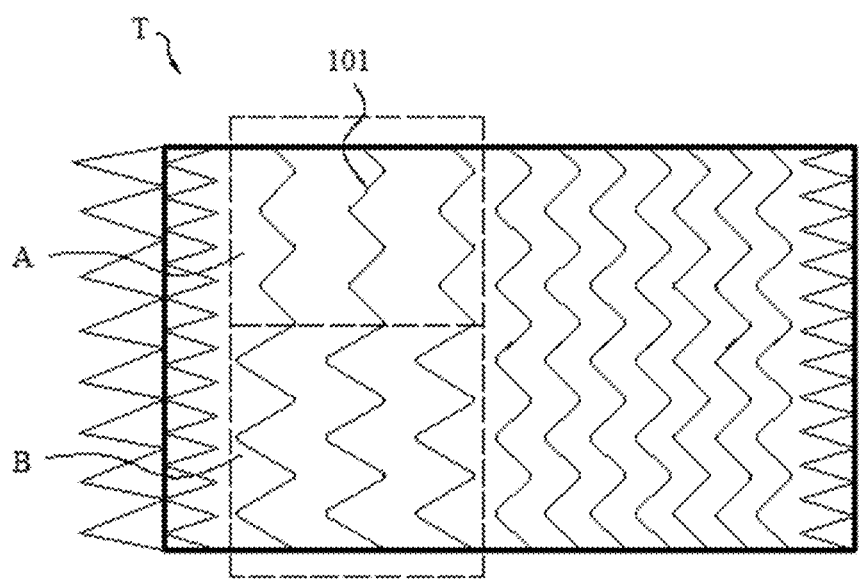
FIG. 4 is a radially expanded view of the stent graft shown in FIG. 3.

As shown in FIG. 3 and FIG. 4, a second exemplary embodiment provides a stent graft, which differs from the first embodiment in that the wave included angle of the first wavy segment is greater than the wave included angle of the second wavy segment, and the wave height of the first wavy segment is less than the wave height of the second wavy segment.

Figure 5:
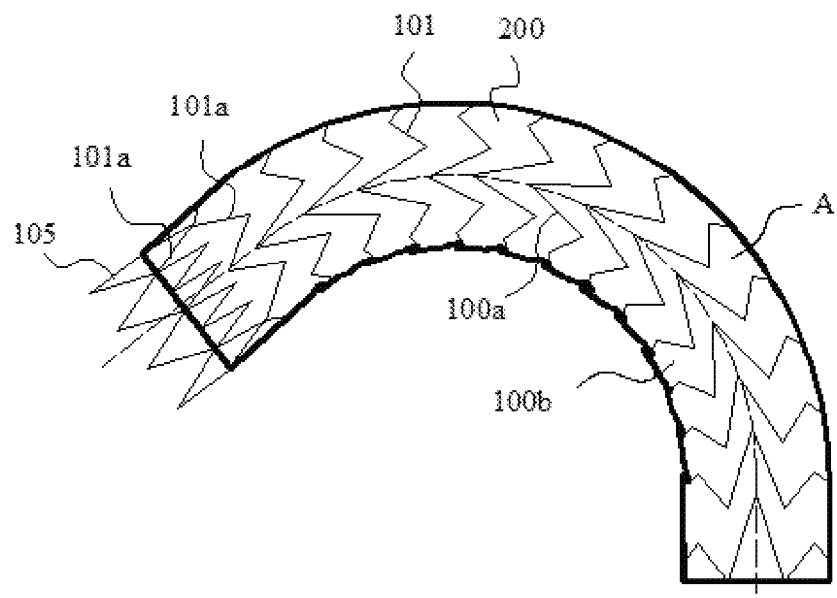
FIG. 5 is a schematic diagram of a straight tubular stent graft provided by a third exemplary embodiment in a bent state.
Figure 6:
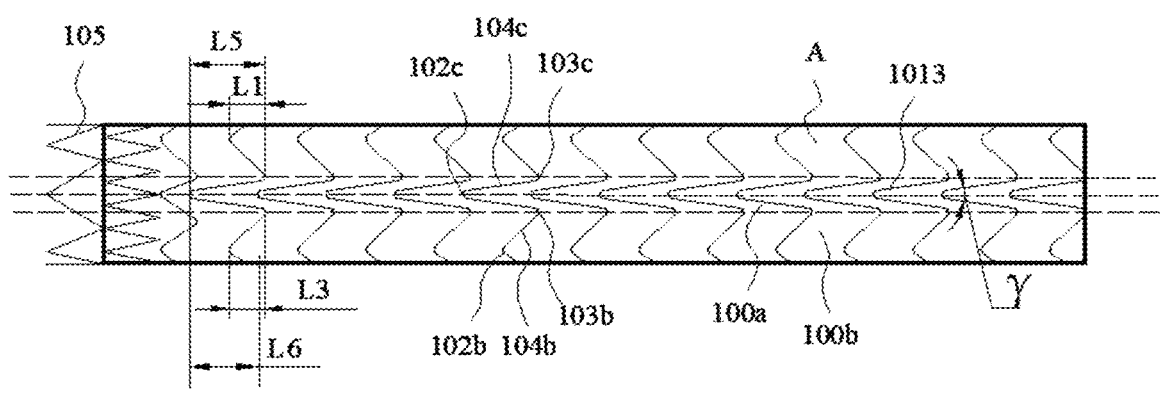
FIG. 6 is a structural schematic diagram of the stent graft shown in FIG. 5 in a natural state.

FIG. 5 shows a stent graft according to a third exemplary embodiment, which differs from the first embodiment in that the region B includes keel regions 100a and non-keel regions 100b that are distributed in the circumferential direction, and the region surrounded by dotted lines in FIG. 6 is the keel region 100a.

The axial shortening rate of the keel region 100a of the stent graft is less than the axial shortening rates of the non-keel region 100b and the region A, and the axial shortening rate of the stent graft in the keel region 100a is 10%-40%.

A method for calculating the shortening rate of the stent graft in the axial direction is as follows. Taking the length of the stent graft, which is in a straight tube shape, along the axial direction in a natural state as r and the diameter of the stent graft as d1, sleeving an inner tube with the diameter of d2 (d2 is less than d1, for example d2 is equal to 90%*d1) out of the stent graft, applying pressure F (1N≤F≤2N) in the axial direction to the stent graft until the stent graft cannot shorten anymore to obtain the total length s of the reel region 100a, and calculating the axial shortening rate of the stent graft in the reel region 100a according to the formula (r−s)/r×100%. Where (r−s) is an available maximum shortening value of the stent graft. The stent graft sleeves the inner tube for shortening, so that the phenomenon that the stent graft is folded when shortening can be effectively avoided, that is, the value of (r−s) is the available maximum shortening value when the stent graft is not folded.

When the stent graft is in a frustum shape, that is, the diameters of the two ends of the stent graft are different, the length of the stent graft in the axial direction in the natural state is r, the diameter of the large end is d1, the diameter of the small end is d3, the stent graft sleeves a conical inner tube or a frustum inner tube with the same taper as the stent graft, and the perpendicular distance between the stent graft and the conical inner tube or the frustum inner tube is 0.05d1. The position of the small end of the stent graft is fixed and unchanged, the pressure F (1N≤F≤2N) in the axial direction is applied to the large end, and the total length of the stent graft when the stent graft cannot shorten anymore is s, and thus the shortening rate of the stent graft in the axial direction is (r−s)/r 100%. The value of (r−s) is an available maximum shortening value of the stent graft. The stent graft sleeves the inner tube for shortening, so that the phenomenon that the stent graft is folded when shortening can be effectively avoided, that is, the value of (r−s) is the available maximum shortening value when the stent graft is not folded.

Figure 7:
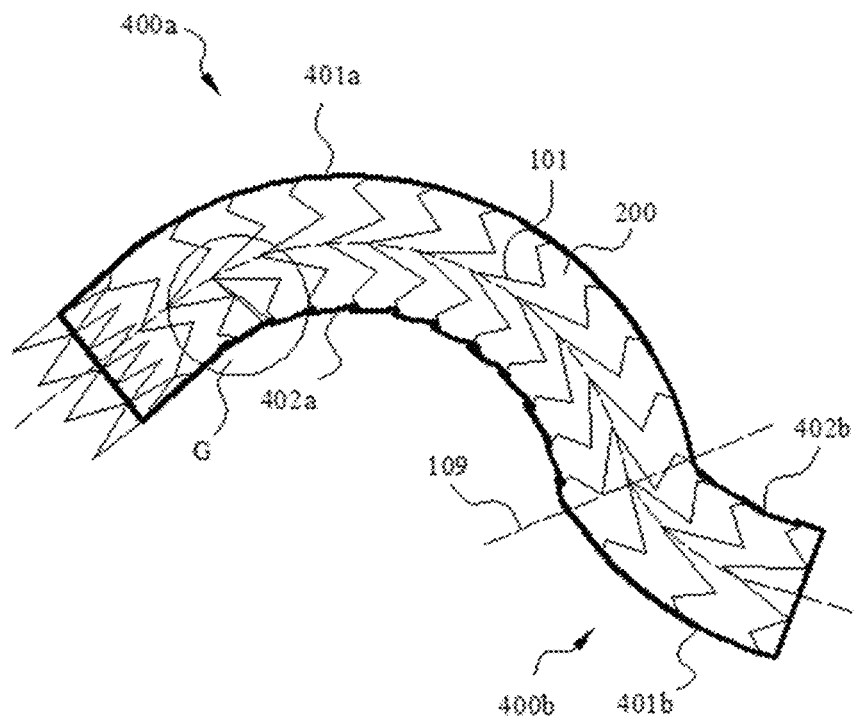
FIG. 7 is a structural schematic diagram of a bent stent graft provided by a third exemplary embodiment.
Figure 8:
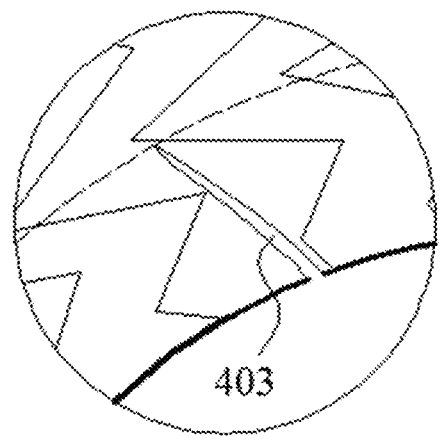
FIG. 8 is an enlarged view of a portion G of the stent graft shown in FIG. 7.
Figure 9:
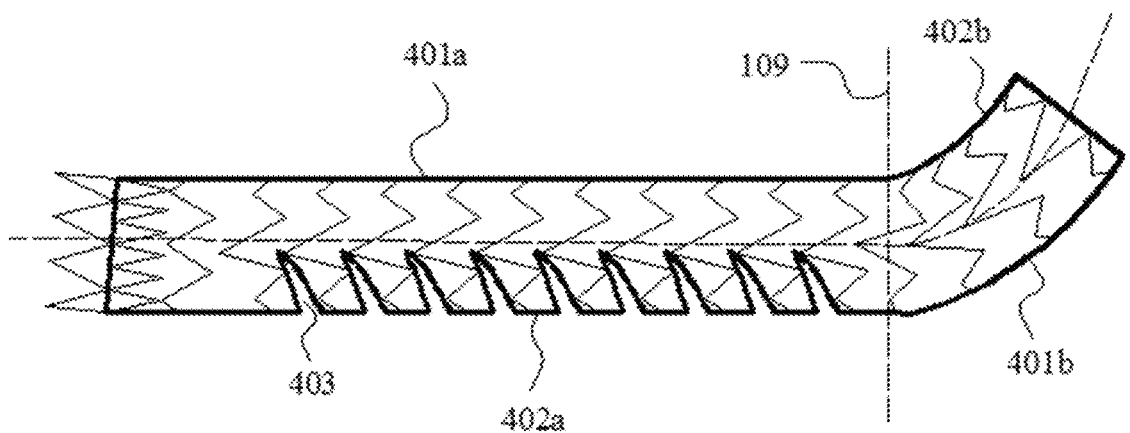
FIG. 9 is a structural schematic diagram of a first bent section of the stent graft shown in FIG. 7 after being straightened along a first profile line.
Figure 10:
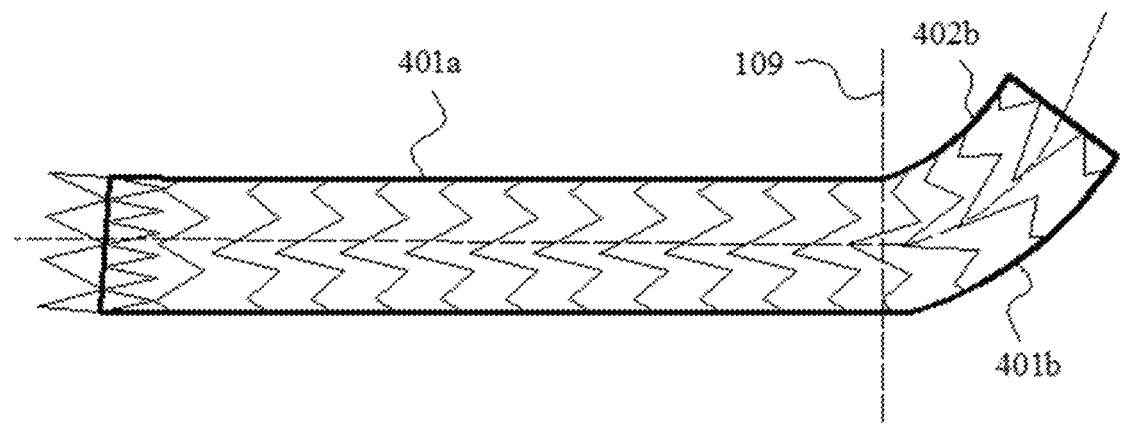
FIG. 10 is a structural schematic diagram of wavy rings of the stent graft shown in FIG. 7 after being re-arranged in the axial direction according to the wave spacing at the first profile line and covered with membranes.

When the stent graft itself is manufactured and shaped into a bent shape, as shown in FIG. 7, the stent graft includes a first bent section 400a and a second bent section 400b, the first bent section 400a has a first profile line 401a on a greater curvature side of the first bent section 400a and a second bent section 402a on a small bent side of the first bent section 400a, and the second bent section 400b has a third profile line 401b on a greater curvature side of the second bent section 400b and a fourth profile line 402b on a small bent side of the second bent section 400b. Two exemplary methods for calculating the shortening rate of the bent section of the stent graft may be provided. One method is as follows: referring to FIG. 8 together, by taking the first bent section 400a as an example, partitioning the first bent section 400a with a plane 109 perpendicular to the axial direction of the stent graft; cutting a plurality of notches 403 in the covering membranes 200 close to the second profile line 402a, where the sizes of the notches 403 can ensure that the stent graft is straightened along the first profile line 401a (or cutting a plurality of notches 403 in the covering membranes 200 close to the second profile line 402a, where the sizes of the notches 403 can exactly ensure that the stent graft is straightened along the first profile line 401a); after the first bent section 400a is straightened as shown in FIG. 9, obtaining the length r and the diameter d1 of the straightened first bent section 400a; sleeving an inner tube with a diameter of d2 (d2 is less than d1, For example d2 is equal to 90%*d1) with the straightened first bent section 400a; applying pressure F (1N≤F≤2N) in the axial direction to the stent graft till the stent graft cannot shorten to obtain the total length s of the region B; and calculating the axial shortening rate of the stent graft in the region B according to the formula (r−s)/r*100%. Another method is as follows: also by taking the first bent section 400a as an example, re-arranging the wavy rings 101 in the axial direction according to the wave spacing between the wavy rings 101 at the first profile line 401a, covering the wavy rings 101 with membranes (covering materials and a selected process are kept consistent with those of the original stent), as shown in FIG. 10, and then calculating the shortening rate according to the above-mentioned method for calculating the shortening rate.

Figure 11:
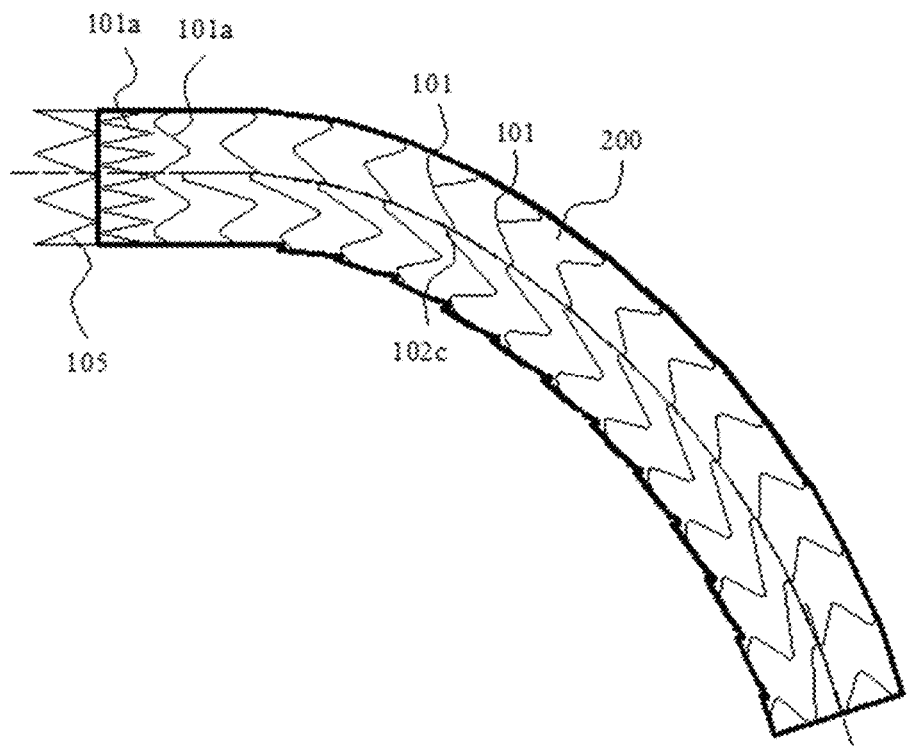
FIG. 11 is a structural schematic diagram of the wavy rings of the stent graft shown in FIG. 5 which abut against mutually.

During the bending of the stent graft, when any one of the keel region 100a, the non-keel region 100b or the region A reaches the available maximum shortening value, a rigid axial supporting structure is formed in the region, so that the stent graft cannot continue to be bent. Referring to FIG. 11, during the bending of the stent graft, one wavy ring 101 of the stent graft moves in the direction of pressure together with portions of the covering membranes 200 fixed to the wavy ring 101, the portions of the covering membranes 200 fixed to the wavy ring 101 move together with portions of the covering membranes 200 distributed at the periphery of the wavy ring 101, immediately the portions of the covering membranes 200 distributed at the periphery of the wavy ring 101 pull another wavy ring 101 nearby to move towards one side close to the wavy ring 101 till the wavy ring 101 cannot keep moving, and at this time a rigid axial supporting structure is formed on the stent graft, so that the stent graft is prevented from continuing to shorten anymore.

When the axial shortening rate of the stent graft in the keel region 100a is less than 10%, the shortening rate of the keel region 100a is too small, and no matter to which direction the stent graft is bent, the keel region 100a easily reaches the available maximum shortening value, and the keel region 100a cannot shorten anymore, thereby restricting the stent graft from continuing to be bent. When the axial shortening rate of the stent graft in the keel region 100a is greater than 40%, the axial supporting effect of the stent graft is poor, and the stent graft may enter the tumor cavity when the distal end of the stent graft shortens towards the proximal end of the stent graft, thus threatening the life of a patient. When the shortening rate of the stent graft in the keel region 100a is 10-40%, the stent graft can be bent towards all directions to adapt to bent blood vessels, and sufficient axial support can be provided for the stent graft to achieve the axial shortening prevention effect, thus maintaining the tube cavity shape of the stent graft. For example, the axial shortening rate of the stent graft in the keel region 100a is 20-30%.

Figure 12:
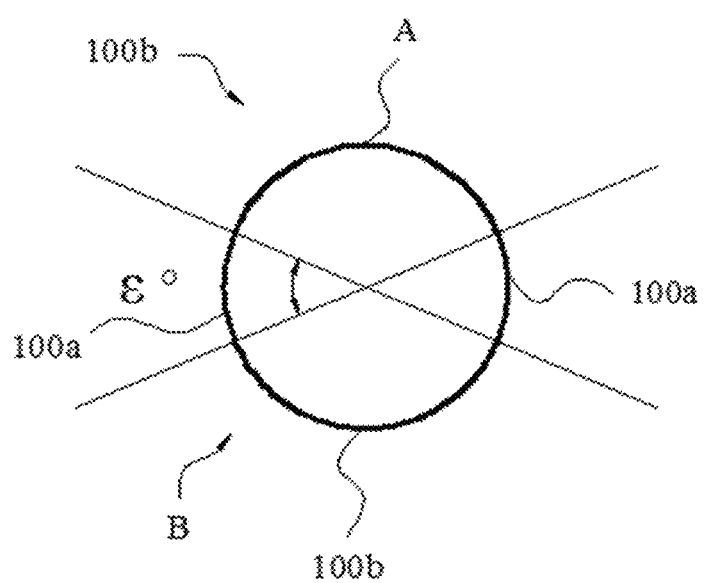
FIG. 12 is a structural schematic diagram of keel regions of the stent graft shown in FIG. 5 that are distributed on an outer surface of the stent graft.

Referring to FIG. 12, the circumferential angle covered by the keel region 100a on an outer surface of the stent graft is ε° which is greater than or equal to 15° and less than or equal to 45°. When ε° is less than 15°, the circumferential angle covered by the keel region 100a on the outer surface of the stent graft is small, so that poor axial supporting effect of the entire stent graft may be caused, and the stent graft may easily swing and retract under the impact of a blood flow, finally causing the stent graft to retract into the tumor cavity, and endangering the life of the patient; and when ε° is greater than 45°, the circumferential angle covered by the keel region 100a on the outer surface of the stent graft is large, which is not conducive to stent bending. When ε° is greater than or equal to 15° and less than or equal to 45°, sufficient axial support can be provided for the stent graft, and when the stent graft is applied to a more bent blood vessel, no folding occurs, thereby keeping the tube cavity smooth, and enabling the stent graft to adapt to a wider range of vascular morphology.

For example, the circumferential angle ε° covered by each keel region 100a on the outer surface of the stent graft is in the range of 20°-30°. In addition, the number of the keel regions 100a is two, and the two keel regions 100a are symmetrically distributed in the circumferential direction of the stent graft.

As shown in FIG. 6, the wavy rings 101 further include third wavy segments 1013 located in the keel region 100a, the wave heights of the third wavy segments 1013 of the keel region 100a being greater than the wave heights of the second wavy segments 1012 of the non-keel region 100b and the wave heights of the first wavy segments 1011 of the region A. The wave height of the first wavy segment 1011 is L1, the wave height of the second wavy segment 1012 is L3, the wave height of the third wavy segment 1013 is L5, and L1, L3 and L5 meet the conditions that L3/L5 is greater than or equal to 1/3 and less than 1 and L1/L5 is greater than or equal to 1/3 and less than 1. When L3/L5 is less than 1/3 or L1/L5 is less than 1/3, dense distribution of local waves in the keel region 100a is easily caused, which affects the bending property of the stent graft in this position, or sparse distribution of local waves in the non-keel region 100b is caused, which results in a poor supporting effect of the stent graft in this position and high probability of deformation.

For example, the second wavy segment 1012 includes at least one second proximal vertex 102b, at least one second distal vertex 103b, and a third supporting body 104b connecting the adjacent second proximal vertex 102b and second distal vertex 103b; and the third wavy segment 1013 includes at least one third proximal vertex 102c, at least one third distal vertex 103c, and a third supporting body 104c connecting the adjacent third proximal vertex 102c and third distal vertex 103c. The wave height L3 of the second wavy segment 1012 refers to the distance in the axial direction between the second proximal vertex 102b and the second distal vertex 103b, and the wave height L5 of the third wavy segment 1013 refers to the distance in the axial direction between the third proximal vertex 102c and the third distal vertex 103c. In the embodiment, the second distal vertex 103b and the third distal vertex 103c are located in the same plane perpendicular to the longitudinal central axis of the stent graft.

Referring to FIG. 6, the distance in the axial direction between the third proximal vertex 102c of the third wavy segment 1013 and a corresponding third proximal vertex 102c of the adjacent wavy ring 101 is L6, where L5 and L6 meet the condition that L6/L5 is greater than or equal to 1/4 and less than or equal to 3/2, so that the wave distribution in the keel region 100a is uniform. For example, L5 is greater than or equal to 8 mm and less than or equal to 18 mm, for example, L5 is greater than or equal to 12 mm and less than or equal to 14 mm.

Since the wavy ring 101 has at least one wave crest with high wave height in the keel region 100a and the plurality of distal vertexes 103 are located in the same plane perpendicular to the longitudinal axis, when the stent graft shortens, the third proximal vertexes 102c on one wavy ring 101 easily abut against another wavy ring 101, and the wavy rings 101 in the keel region 100a abut against mutually; and when the wavy rings 101 in the keel region 100a abut against mutually, a rigid axial supporting structure is formed on the stent graft to prevent the stent from continuing to shorten. By arranging the keel regions 100a on the stent graft, various bending requirements of the stent graft can be met, and sufficient axial supporting force can be provided for the stent graft, thereby preventing the stent graft from shortening into the tumor cavity. Since the wave height of the third wavy segment 1013 of the keel region 100a is greater than the wave height of the second wavy segment 1012 of the non-keel region 100b and the wave height of the first wavy segment 1011 of the region A, that is, the coverage rate of the wavy rings in the keel region 100a is relatively high, the relatively low coverage rate of wavy rings may be set in the non-keel region 100b to enable the non-keel region 100b to meet the fenestration requirement of the stent graft. For example, the ratio of the wave height of the second wavy segment 1012 of the non-keel region 100b to the wave height of the first wavy segment 1011 of the region A is 0.8-1.2, and the ratio of the spacing between two adjacent second wavy segments to the spacing between two adjacent first wavy segments is 0.8-1.2.

In an embodiment, the third wavy segments 1013 include a third proximal vertexes 102c, the connecting lines between the third proximal vertexes 102c of the adjacent third wavy segments 1013 are parallel to the axis of the stent graft, and the wave included angles γ of the third wavy segments 1013 are less than the wave included angles α of the first wavy segments 1011 and the wave included angles β of the second wavy segments 1012.

The wave shapes, the number of waves, the wave heights, and the wave included angles of the third wavy segments and the second wavy segments may be set as desired. For example, the third wavy segment has one V-shaped wave with a wave included angle 30°-40° and a wave height 12-14 mm. The second wavy segment has 3 to 5 V-shaped waves with a wave included angle of 60°-70° and a wave height 6-10 mm.

Further, referring to FIG. 5, at least one proximal wavy ring 101a is disposed at one end of the plurality of wavy rings 101.

The axial shortening rate between the proximal wavy ring 101a and its adjacent wavy ring 101 is less than 10%, so as to enhance the axial supporting effects of end portions of the stent graft, and prevent the two ends of the stent graft from causing the stent graft to swing under the impact of the blood flow.

When the number of the proximal wavy rings 101a is at least two, the axial shortening rate between the at least two proximal wavy rings 101a is less than 3%, so as to enhance the axial supporting effects of end portions of the stent graft, and prevent the end portions of the stent graft from causing the stent graft to swing under the impact of the blood flow. For example, the axial shortening rate between the at least two proximal wavy rings 101a is zero.

Figure 13:
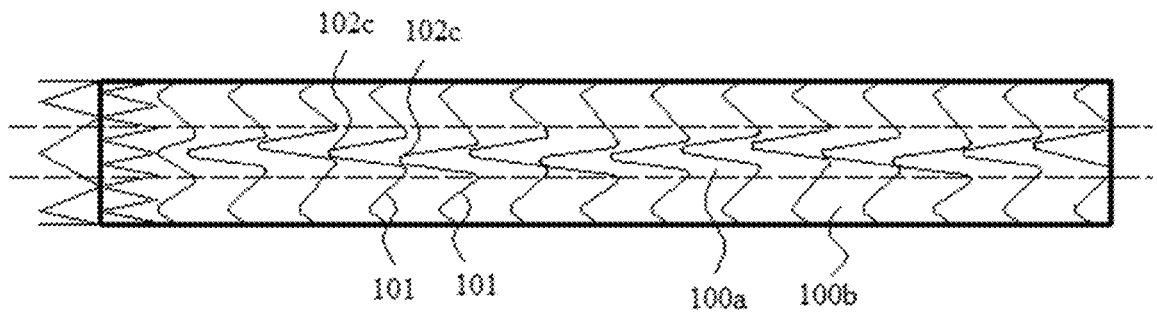
FIG. 13 is a schematic diagram of a stent graft provided by a fourth exemplary embodiment.

FIG. 13 shows a stent graft provided by a fourth exemplary embodiment, which differs from the third embodiment in that a connecting line between the third proximal vertexes 102c of the adjacent third wavy segments is disposed obliquely with respect to the axis of stent graft.

Figure 14:
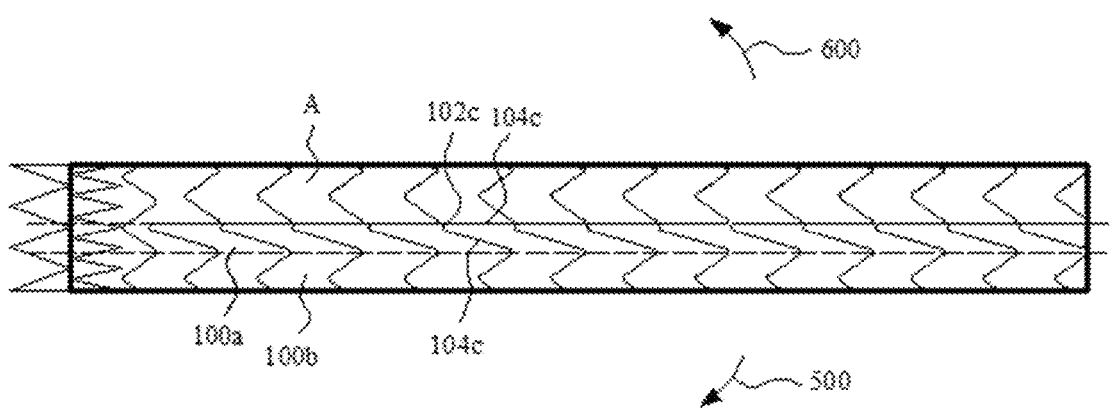
FIG. 14 is a schematic diagram of a stent graft provided by a fifth exemplary embodiment.

FIG. 14 shows a stent graft provided by a fifth exemplary embodiment, which differs from the third embodiment in that the third supporting bodies 104c that are connected to one sides of the third proximal vertexes 102c and close to the region A are distributed in the axial direction parallel to the stent graft, and the third supporting bodies 104c that are connected to the other sides of the third proximal vertexes 102c and close to the non-keel region 100b are disposed obliquely with respect to the axis direction of the stent graft.

Figure 15:
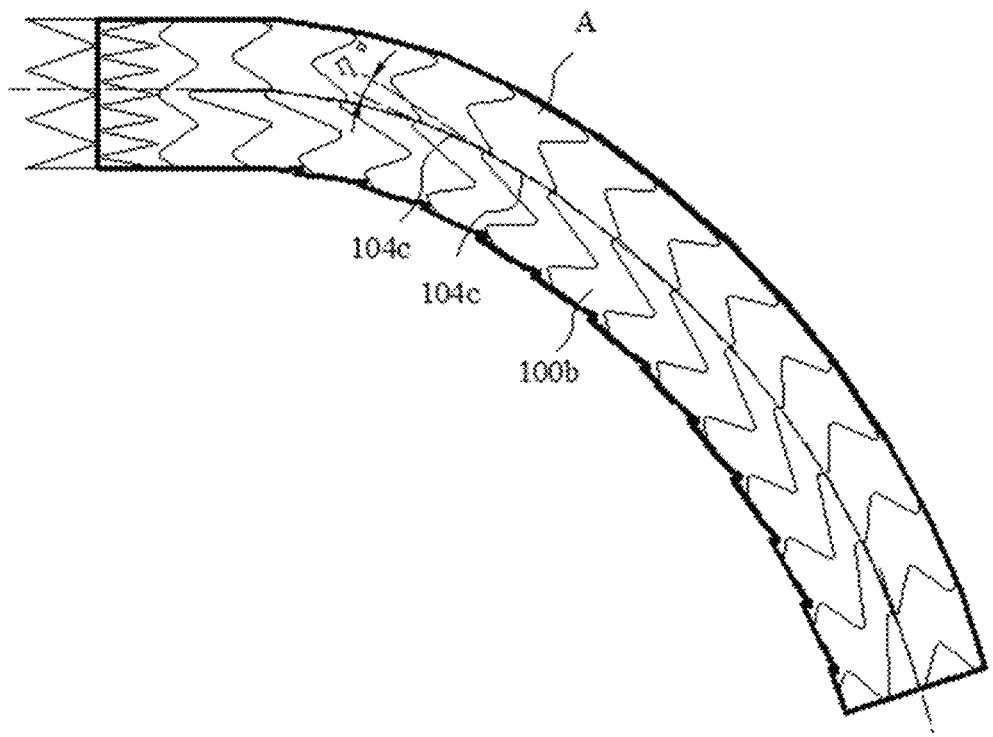
FIG. 15 is a structural schematic diagram of the stent graft shown in FIG. 14 after being bent in a direction indicated by a first arrow.
Figure 16:
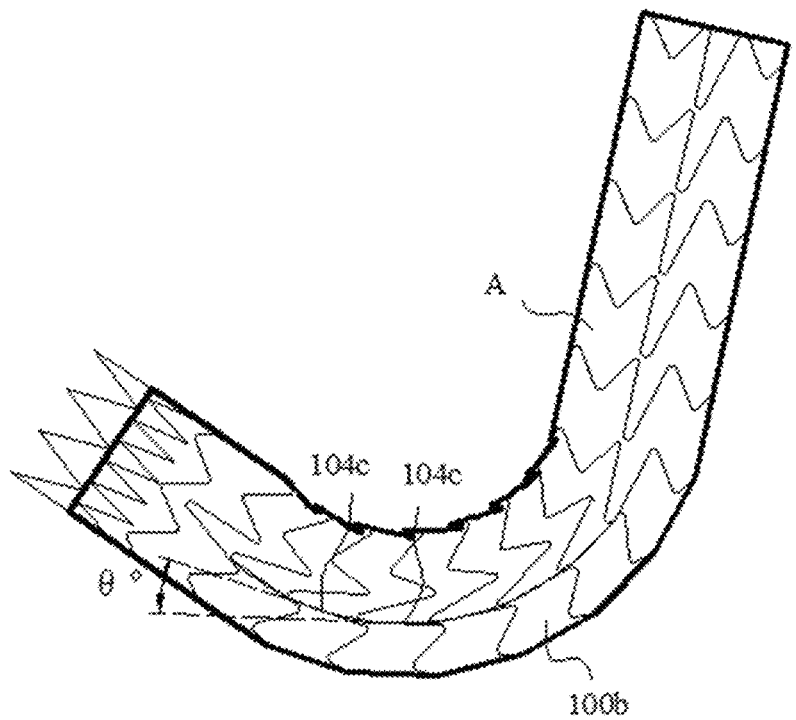
FIG. 16 is a structural schematic diagram of the stent graft shown in FIG. 14 after being bent in a direction indicated by a second arrow.

When the stent graft shown in FIG. 14 is bent in a direction indicated by a first arrow 500, referring to FIG. 15, the third supporting bodies 104c of the adjacent third wavy segments adjacent to the region A abut against mutually to form an axial support, and the included angle between the third supporting bodies 104c of the adjacent third wavy segments adjacent to the region A is η°. When the stent graft shown in FIG. 14 is bent in a direction indicated by a second arrow 600, referring to FIG. 16, the third supporting bodies 104c of the adjacent third wavy segments adjacent to the non-keel region 100b abut against mutually to form an axial support, and the included angle between the third supporting bodies 104c of the adjacent third wavy segments adjacent to the non-keel region 100b is θ°. As can be seen from the figures, η° is less than θ°. When the third supporting bodies 104c of the adjacent third wavy segments abut against mutually to form the axial support, the greater the included angle between the third supporting bodies 104c of the adjacent third wavy segments is, the smaller the force resolved to the axial direction of the stent graft is, and the poorer the axial supporting effect on the stent graft is. Therefore, the axial supporting effect formed when the third supporting bodies 104c distributed in the axial direction parallel to the stent graft abut against mutually in FIG. 15 is superior to the axial supporting effect formed when the third supporting bodies 104c disposed obliquely with respect to the axis direction of the stent graft abut against mutually in FIG. 16. Meanwhile, when the included angle between the third supporting bodies 104c of the adjacent third wavy segments is greater, excessive deformation of the covering membranes of the keel regions 100a is easily caused to bring about an uneven surface of the stent graft, thus leading to high probability of thrombosis.

When the third supporting bodies 104c distributed in the axial direction parallel to the stent graft abut against mutually to form the axial support, the included angle between the third supporting bodies 104c of the adjacent third wavy segments is minimum, and the axial supporting force of the stent graft is maximum. Therefore, the third supporting bodies 104a distributed in the axial direction parallel to the stent graft are disposed on one side close to the region A, and when the stent graft is bent towards the side of the non-keel region 100b, the third supporting bodies may provide sufficient axial supporting force for the stent graft, the axial supporting effect on the stent graft is optimal, and the fenestration may be carried out in the region A.

The features of the above-mentioned embodiments may be combined in any combination. In the interest of brevity, all possible combinations of the technical features in the above embodiments are not described, but all should be considered as within the scope, except combinations where at least some of such technical features are mutually exclusive.

The above-mentioned embodiments are merely illustrative of several embodiments of the present application, and the description thereof is not to be construed as limiting the scope of protection of the present application. It should be noted that several modifications and improvements can be made by those of ordinary skill in the art without departing from the concept of the present application, which fall within the scope of protection of the present application.

The invention claimed is:

1. A stent graft, comprising: at least one region T disposed along an axial direction of the stent graft, the region T is partitioned by two planes p1 and p2; the region T comprises a plurality of wavy rings, each wavy ring is a closed cylindrical structure, and comprises a plurality of proximal vertices, a plurality of distal vertices, and supporting bodies connecting the adjacent proximal vertices, and distal vertices; the region T with the plurality of wavy rings is divided into at least, in a circumferential direction, a region A partitioned by said two planes p1 and p2 and a region B partitioned by said two planes p1 and p2 connected with the region A from said plane p1 to said plane p2, such that each of the regions T, A, and B is bounded in the axial direction of the stent graft by the two planes p1 and p2;

each of the region A and region B comprises the wavy rings in a corresponding region of the region T; wherein a ratio of an area of the region A to an area of the region T ranges from 1/4 to 2/3; a ratio of a coverage rate of the wavy rings in the region A to a coverage rate of the wavy rings in the region B ranges from 1/5 to 9/10; and a ratio of a coverage rate of the wavy rings in each circular region with a diameter of 20 mm within the region A to the coverage rate of the wavy rings in the region A ranges from 0.7 to 1.3; wherein each circular region with a diameter of 20 mm within the region A is a two-dimensional circular region randomly defined in the region A, and the two-dimensional circular region has a diameter of 20 mm and comprises the wavy rings in a corresponding region of the region A; and wherein the area of region A is larger than an area of each circular region with a diameter of 20 mm within region A, and the coverage rate of the wavy rings in each region is calculated in a way that a surface area of the wavy rings projected onto an inner wall of a tube cavity of the stent graft in the each region is divided by a surface area of the corresponding inner wall of the tube cavity of the stent graft in the each region and multiplied by 100.

2. The stent graft of claim 1, wherein the ratio of the area of the region A to the area of the region T ranges from 1/3 to 1/2; the ratio of the coverage rate of the wavy rings in the region A to the coverage rate of the wavy rings in the region B ranges from 2/5 to 9/10; and the ratio of the coverage rate of the wavy rings in each circular region with the diameter of 20 mm within the region A to the coverage rate of the wavy rings in the region A ranges from 0.9 to 1.1.

3. The stent graft of claim 2, wherein that the region A comprises a plurality of first wavy segments of the plurality of wavy rings, arranged in a spaced manner along the axial direction, a wave height of each of the plurality of first wavy segments is L1, a spacing between adjacent first wavy segments of the plurality of first wavy segments is L2, and L1/L2 is greater than or equal to 1/4 and less than or equal to 3.

4. The stent graft of claim 3, wherein L1 is greater than or equal to 4 mm and less than or equal to 12 mm.

5. The stent graft of claim 3, wherein all wave heights of the plurality of first wavy segments are equal, and all spacings between adjacent first wavy segments of the plurality of first wavy segments are equal.

6. The stent graft of claim 3, wherein the region B comprises keel regions and non-keel regions that are distributed along the circumferential direction, each non-keel region comprises a plurality of second wavy segments distributed along the axial direction, each keel region comprises a plurality of third wavy segments distributed along the axial direction, and all wave heights of the plurality of third wavy segments are greater than all wave heights of the plurality of first wavy segments and all wave heights of the plurality of second wavy segments.

7. The stent graft of claim 6, wherein a ratio of a wave height of each of the plurality of second wavy segments to the wave height of each of the plurality of first wavy segments ranges from 0.8 to 1.2, and a ratio of a spacing between adjacent second wavy segments of the plurality of second wavy segments to the spacing between the adjacent first wavy segments of the plurality of first wavy segments ranges from 0.8 to 1.2.

8. The stent graft of claim 6, wherein a wave included angle of each of the plurality of third wavy segments is less than a wave included angle of each of the plurality of first wavy segments and a wave included angle of each of the plurality of second wavy segments.

9. The stent graft of claim 6, wherein a circumferential angle covered by the keel region on an outer surface of the stent graft is greater than or equal to 15° and less than or equal to 45°.

10. The stent graft of claim 3, wherein the stent graft further comprises at least one proximal wavy ring located at one end of the region T, and at least one distal wavy ring located at a second end of the region T, respectively.

11. The stent graft of claim 10, wherein a coverage rate of the wavy rings in a region where the at least one proximal wavy ring is located is greater than a coverage rate of the plurality of wavy rings in the region T, and a coverage rate of wavy rings in a region where the at least one distal wavy ring is located is greater than the coverage rate of the plurality of wavy rings in the region T.

12. The stent graft of claim 11, wherein the stent graft further comprises at least one non-end wavy ring located between the plane p2 and the distal wavy ring, and a coverage rate of wavy rings in a region where the at least one non-end wavy ring is located is greater than a coverage rate of the plurality of wavy rings in the region T, the stent graft further only comprises one proximal wavy ring located at one end of the region T, and one distal wavy ring located at a second end of the region T, the proximal wavy ring, the non-end wavy ring, and the distal wavy ring are of closed cylindrical structures.

13. The stent graft of claim 2, wherein the plurality of wavy rings in region T are sequentially arranged along the axial direction in a spaced manner without any metal wire connecting with each other.

14. The stent graft of claim 1, wherein the stent graft further comprises an anchoring bare stent located at at least one end of the stent graft.

15. The stent graft of claim 1, wherein the plurality of wavy rings of the region T comprises a first wavy segment located in the region A, where the first wavy segment includes a plurality of first proximal vertices of the plurality of proximal vertices, a plurality of first distal vertices of the plurality of distal vertices, and first supporting bodies of the supporting bodies, the first supporting bodies connecting adjacent first proximal vertices and first distal vertices.

16. The stent graft of claim 15, wherein the plurality of first distal vertices are located in a plane which is perpendicular to a longitudinal axis of the stent graft.

17. The stent graft of claim 15, wherein the wavy ring in the region T further comprises a second wavy segment located in the region B, a wave included angle of the first wavy segment is greater than a wave included angle of the second wavy segment, and a wave height of the first wavy segment is the same as a wave height of the second wavy segment.

18. The stent graft of claim 1, wherein the region A comprises a plurality of first wavy segments of the plurality of wavy rings, arranged in a spaced manner along the axial direction, and a phase difference between two adjacent first wavy segments is 0-45°.

19. The stent graft of claim 1, wherein the region A comprises a plurality of first wavy segments arranged in a spaced manner along the axial direction, the region B comprises a plurality of second wavy segments arranged in a spaced manner along the axial direction, and the number of the plurality of the first wavy segments in region A is equal to the number of the plurality of the second wavy segments in region B.

20. A stent graft, comprising: at least one region T disposed along an axial direction of the stent graft, the region T is partitioned by two planes p1 and p2; the region T comprises a plurality of wavy rings, each wavy ring is a closed cylindrical structure, and comprises a plurality of proximal vertices, a plurality of distal vertices, and supporting bodies connecting the adjacent proximal vertices and distal vertices; the region T with the plurality of wavy rings is divided into at least, in a circumferential direction, a region A partitioned by said two planes p1 and p2 and a region B partitioned by said two planes p1 and p2 connected with the region A from said plane p1 to said plane p2; and each of the region A and region B comprises the wavy rings in a corresponding region of the region T; wherein a ratio of an area of the region A to an area of the region T ranges from 1/4 to 2/3; a ratio of a coverage rate of the wavy rings in the region A to a coverage rate of the wavy rings in the region B ranges from 1/5 to 9/10; and a ratio of a coverage rate of the wavy rings in each circular region with a diameter of 20 mm within the region A to the coverage rate of the wavy rings in the region A ranges from 0.7 to 0.9, or from 1.1 to 1.3;

wherein each circular region with a diameter of 20 mm within the region A is a two-dimensional circular region randomly defined in the region A, and the two-dimensional circular region has a diameter of 20 mm and comprises the wavy rings in a corresponding region of the region A; and wherein the area of region A is larger than an area of each circular region with a diameter of 20 mm within region A, and the coverage rate of the wavy rings in each region is calculated in a way that a surface area of the wavy rings projected onto an inner wall of a tube cavity of the stent graft in the each region is divided by a surface area of the corresponding inner wall of the tube cavity of the stent graft in the each region and multiplied by 100;

wherein the plurality of wavy rings of the region T comprises a first wavy segment located in the region A, where the first wavy segment includes a plurality of first proximal vertices of the plurality of proximal vertices, a plurality of first distal vertices of the plurality of distal vertices, and first supporting bodies of the supporting bodies, the first supporting bodies connecting adjacent first proximal vertices and first distal vertices; and wherein the plurality of wavy rings of the region T further comprises a second wavy segment located in the region B, a wave included angle of the first wavy segment is greater than a wave included angle of the second wavy segment, and a wave height of the first wavy segment is the same as a wave height of the second wavy segment;

wherein the stent graft further comprises one proximal wavy ring located at one end of the region T, and one distal wavy ring located at a second end of the region T, respectively;

wherein a coverage rate of the wavy rings in a region where the at least one proximal wavy ring is located is greater than a coverage rate of the plurality of wavy rings in the region T, and a coverage rate of wavy rings in a region where the at least one distal wavy ring is located is greater than the coverage rate of the plurality of wavy rings in the region T;

wherein the stent graft further comprises at least one non-end wavy ring located between the plane p2 and the distal wavy ring, and a coverage rate of wavy rings in a region where the at least one non-end wavy ring is located is greater than a coverage rate of the plurality of wavy rings in the region T, the proximal wavy ring, the non-end wavy ring, and the distal wavy ring are of closed cylindrical structures.

* * * * *